US011344203B2

(12) United States Patent
Huber

(10) Patent No.: US 11,344,203 B2
(45) Date of Patent: May 31, 2022

(54) OPTO ACOUSTIC DEVICE SYSTEM AND METHOD

(71) Applicant: Arie Huber, Haifa (IL)

(72) Inventor: Arie Huber, Haifa (IL)

(73) Assignee: PRC CARDIO OPTIC LTD., Haifa (IL)

( * ) Notice: Subject to any disclaimer, the term of this patent is extended or adjusted under 35 U.S.C. 154(b) by 0 days.

(21) Appl. No.: 16/761,311

(22) PCT Filed: Sep. 15, 2018

(86) PCT No.: PCT/IB2018/057089
§ 371 (c)(1),
(2) Date: May 4, 2020

(87) PCT Pub. No.: WO2019/097317
PCT Pub. Date: May 23, 2019

(65) Prior Publication Data
US 2020/0375468 A1     Dec. 3, 2020

Related U.S. Application Data

(60) Provisional application No. 62/588,387, filed on Nov. 19, 2017, provisional application No. 62/597,059, filed on Dec. 11, 2017.

(51) Int. Cl.
*A61B 5/00* (2006.01)
*A61B 5/02* (2006.01)

(52) U.S. Cl.
CPC .......... *A61B 5/0084* (2013.01); *A61B 5/0095* (2013.01); *A61B 5/02007* (2013.01)

(58) Field of Classification Search
CPC ....... A61B 5/00; A61B 5/0084; A61B 5/0095; A61B 5/02007
See application file for complete search history.

(56) References Cited

U.S. PATENT DOCUMENTS

2004/0054268 A1*  3/2004  Esenaliev .......... A61B 5/14535
                                                      600/322
2006/0184042 A1   8/2006  Wang et al.
(Continued)

FOREIGN PATENT DOCUMENTS

| WO | 2011150379  | 12/2011 |
| WO | 2017167762  | 10/2017 |
| WO | 2019/097317 | 5/2019  |

OTHER PUBLICATIONS

International Search Report for Application PCT/IB2018/057089, dated Apr. 30, 2019.
(Continued)

*Primary Examiner* — Joel F Brutus
(74) *Attorney, Agent, or Firm* — The Law Office of Joseph L. Felber

(57) ABSTRACT

A system is provided for scanning organs in a human body, preferably a human's cardiovascular system more preferably the heart and other arteries. The system includes an extracorporeal opto-acoustic scanning device for scanning from outside of the body and optionally in correlation to inside optic imaging Both comprise a laser or other opto acoustic light and a transducer. The laser being arranged to emit laser pulses towards and/or into the organ system and the transducer being arranged to detect acoustic waves received back from the organ system for imaging the scanned tissue.

13 Claims, 3 Drawing Sheets

(56) References Cited

U.S. PATENT DOCUMENTS

| | | |
|---|---|---|
| 2006/0287590 A1 | 12/2006 | McEowen |
| 2007/0276226 A1 | 11/2007 | Tal |
| 2010/0198081 A1 | 8/2010 | Hanlin et al. |
| 2013/0338498 A1* | 12/2013 | Emelianov ............... A61B 8/12 600/431 |
| 2014/0194704 A1* | 7/2014 | Millett ................ A61B 8/4483 600/301 |
| 2015/0272445 A1 | 10/2015 | Rozental et al. |
| 2017/0043128 A1* | 2/2017 | Hu ....................... A61B 8/0841 |
| 2017/0143236 A1* | 5/2017 | Shekhar ............... A61B 8/5207 |

OTHER PUBLICATIONS

Written Opinion for Application PCT/IB2018/057089, dated Apr. 30, 2019.

\* cited by examiner

OPTO ACOUSTIC DEVICE SYSTEM AND METHOD

TECHNICAL FIELD

Embodiments of the invention relate to an opto-acoustic device system and/or method, in particular for scanning body vasculature and/or therapeutic devices within a body vasculature.

BACKGROUND

Minimally invasive procedures for treating a body vasculature or bodily vessel may include delivering interventional, diagnostic and/or therapeutic devices, e.g. over guide wires, to a location within the bodily vessel. Such catheters may typically be arranged for introduction into the body through a natural or artificial orifice formed in the body.

Known minimal invasive procedures making use of therapeutic devices in form of catheters may include procedures for deploying stents to alleviate coronary blood vessel blockages, referred to as "stenosis", resulting from thromboses (blood clots) or the buildup of plaque that restricts or block blood flow. Other example of therapeutic devices typically used may include imaging catheters such as those used in intravascular ultrasound (IVUS) and intracardiac echocardiography (ICE) applications.

X-ray-based imaging techniques are typically used in conjunction with radiopaque contrast dye in order to guide therapeutic devices; such as guide wires catheters (or the like) to a region of the body to be treated.

Radiopaque contrast dye is used to enhance the visibility of internal structures by absorbing external X-rays, resulting in decreased exposure on the X-ray detector. Use of radiopaque contrast dye however may have adverse effects such as thyreotoxicosis or hypersensitivity reactions.

Opto-acoustic imaging is an imaging technology typically used in certain therapeutic procedures, such as in detection of breast cancer. Opto-acoustic imaging involves delivery of laser pulses into biological tissues, which are absorbed and converted into heat leading to ultrasonic emission. The generated ultrasonic waves are then detected by ultrasonic transducers and analyzed to produce images.

US2013109950 for example describes an opto-acoustic device includes that a probe connected via a light path and an electrical path to a system chassis that includes a light subsystem and a computing subsystem. The computing subsystem includes one or more computing components for ultrasound control and analysis and opto-acoustic control and analysis.

SUMMARY

The following embodiments and aspects thereof are described and illustrated in conjunction with systems, tools and methods which are meant to be exemplary and illustrative, not limiting in scope.

An aspect of at least certain embodiments of the invention relates to an embodiment of an extracorporeal opto-acoustic device and/or to a method and/or use of such an extracorporeal device that is situated outside the body—for detecting, scanning and/or viewing body vasculature and/or therapeutic devices within a body vasculature.

Possibly, such body vasculature may include coronary blood vessels (or the like) and therapeutic devices within such vessels may be those e.g. suitable for angioplasty procedures such as catheters, guidewires or any other therapeutic device or system navigated into and/or used within such vessels by a physician.

In at least certain cases, methods deploying use of extracorporeal opto-acoustic device embodiments may be arranged, suited and/or tuned to detect specific regions of therapeutic devices within a body vasculature, such as tip regions of such therapeutic devices (or the like). Possibly, detection of such specific regions may be embodied by such therapeutic devices being arranged to include tailored-markers as detailed below, In at least certain cases, such detection of certain regions within therapeutic devices may be facilitated or enabled by choice of suitable materials deposited or formed within regions of the therapeutic devices that form distinct acoustic signals when scanned by various opto-acoustic device embodiments.

Possibly, to be scanned therapeutic devices within a body vasculature may be fitted with imaging technology such as those used in intravascular ultrasound (IVUS) and intracardiac echocardiography (ICE) applications. Possibly, such imaging technology may include opto-acoustic technology permitting e.g. forward looking when positioned on a tip region of a therapeutic device.

Use of extracorporeal opto-acoustic devices for scanning body vasculature and/or therapeutic devices within such body vasculature—may be performed with administration of substantially none or minimum contrast clay material into a patient's vasculature. Possibly, therapeutic devices scanned may be the guidewire or catheter and scanned data may relate to position preferably at any time while substantially not using any dosage of contrast clay material or using only relative smaller amounts of such contrast agent relative to amounts of contrast agent required under scanning techniques such as those utilizing x-ray. Possibly internal catheters comprising embodiments of opto-acoustic devices may be integrated with cleaning tools or devices and/or steering tools.

Possibly, bodily tissue material typically scannable by opto-acoustic technology or material resembling same—may be implanted within/upon internal therapeutic devices, such as catheter (or the like)—in order to act as so-called tailored-markers (such as e.g. opaque markers detectable under X-ray).

In at least certain embodiments, a system including an extracorporeal opto-acoustic device may include transducer, electronic, mechanical opto-acoustic components, fiber optics, and a display.

In an aspect, at least certain embodiments of the present invention provide in combination an imaging probe assembled on a catheter or guide wire head providing forward visualization e.g. into occluded artery and a non-invasive external scanning instrument for visualizing the anatomy proximal to the catheter or guide wire position and/or the catheter or guide wire itself—where such external scanning is possibly performed using minimal or substantially no contrast material within the scanned bodily vessel.

Possibly, such imaging probe providing e.g. forward looking and utilizing opto-acoustic or photo-acoustic technology—may be arranged to emit laser pulses that are suited e.g. to penetrate into blockages—and based on acoustic waves reflections back from the tissue—a distance calculation, width, material density (or the like) relating to the scanned tissue may be computed possibly on an adjacent external accompanying software/computer.

Possibly, catheters used in such system in addition or instead to imaging capability may be integrated or include capabilities for opening and/or cleaning e.g. plaque from arteries or veins in which they are deployed as well as steering capabilities of catheters or guide wires.

An aspect of at least certain embodiments of the invention thus relates to provision of full imaging e.g. for angioplasty procedures—namely imaging by external opto-acoustic device combined with internal imaging device located within a bodily vessel.

In addition or alternatively, internal therapeutic devices within a body vasculature may be suited for chronic total occlusion procedures, safely performing same with minimal or substantially no use of the contrast material within a patient's artery.

Possibly, visualization within an occluded artery and in particular by the external opto-acoustic device may be performed under regulated energy management, thus saving on energy. Such saving on energy may be embodied by delivery of laser pulses into biological tissues, where possibly further energy saving may be obtained by regulating the number of pulses, their intensity and/or pauses between pulses admitted to biological tissues.

In one aspect, an imaging system may be provided integrated with opening, cleaning and steering technologies and capabilities for provision of real time imaging during a therapeutic procedure administered by a catheter or guidewire.

Such imagining may facilitate detection of position and location within an artery and possibly forward looking if internal device is equipped with suitable imaging technology, where possibly said forward looking is a few centimeters ahead into the vessel to possibly ensure safe procedure, while substantially eliminating need for use of contrast dye material during procedure.

Possibly, such system may include on a tip of its internal catheter or guide wire, a sensor that may comprise a laser acoustic or other photo acoustic imaging inside the blood.

In order ensure better real time imaging—embodiments of the system may include separate non-invasive imaging tool to follow the sensor or the catheter head position and location by using laser acoustic technologies combined with external imaging to provide a 3D mapping of the vessel or organ treated.

In one embodiment, the invasive head within an imaging system may include, an invasive sensor integrated on a guide wire, that may be embodied as a converted transducer, optical fibers, micro servo and other features to permit provision of short laser pulses and conversion of ultrasound real time images on an external display.

In at least certain embodiments, external and/or internal opto/photo-acoustic device may generate an ultrasonic signal in response to laser light transmitted along a plurality of optical fibers into the bodily vessel and towards body tissue.

Catheters typically include a port located towards their proximal end, for possibly receiving a guidewire and admitting it into a bodily vessel—and may also include a coupler at their proximal end to which a console may typically be attachable—and possibly fibers for transmitting laser pulses towards bodily tissue to be scanned may extend through such port and/or console.

In order to eliminate or significantly reduce contrast dye material, a parallel non-invasive tool using laser acoustic or other photo-acoustic real time imaging, may be processed to image and control the catheter or guide wire head location and position.

Possibly, 3D images and/or data visualizing scanned/imaged data from within and outside the bodily vessel, by internal and external opto-acoustic devices, respectively—may be integrated possibly in real-time for purposes of display for a physician.

Possibly such images/scans or 3D reconstructed data may be of views ahead and/or aside of an internal catheter located within the bodily vessel, possibly of the artery. Possibly, laser acoustic energy may also be utilized for melting chronic total occlusion in the artery.

Possibly opto-acoustic scanning may be defined or facilitated by relative short pulses of laser light energy, possibly at a specific wavelength (color), directed at and illuminating a large volume of tissue in a selected region. Heat created at the tissue may result in thermoelastic expansion of the structure generating a sound pressure wave which is captured by wideband, ultrasonic, piezoelectric transducer.

A reconstruction algorithm may determine the spatial location of optical data absorbed from the captured data. Such reconstruction, possibly, 3D reconstruction, may be executed using methods such as Semantic Segmentation including analysis of pixel by pixel and pattern recognition technologies.

In an aspect, the present invention may be defined as an internal imaging probe assembled on a catheter or guide wire or other carrier that may be inserted within an artery for angioplasty and treatment procedure. Possibly said probe may be arranged to generate real time imaging, possibly 3D imaging, presented on an external display, of the artery sides and walls and possibly 1-5 centimeters forward looking possibly into a chronic total occlusion or in the artery lumen.

Possibly, the imaging probe may be integrated with tools to open and clean plaque or Chronic Total Occlusion and steering the probe tip, where said forward looking imaging may utilize laser-acoustic or other photo-acoustic technologies.

In certain embodiments, an imaging probe assembled on catheter or guide wire or other carrier arranged for insertion inside an artery for angioplasty and treatment procedure may be suited to generate, possibly in real time, image or video on an external display.

Preferably, an external device utilizing opto-acoustic or photo-acoustic technology may be suited to simultaneously scan/image internal organs, such as internal blood vessels, possibly same vessels in which the internal device is located—while substantially not using contrast dye material during such scanning/imaging procedures.

Possibly, the external non-invasive instrument/device may provide real time imaging or video on an external display of the head of the catheter or Guide wire location and the arteries, while substantially eliminating need for the contrast material—otherwise required when external technology utilized possible relies on X-ray.

Possibly, an external non-invasive instrument/device using photo-acoustic or opto-acoustic method for generating 2 and/or 3 Dimensions real time imaging or video on an external display—may provide same on a position of the head of the catheter or the guide wire location and position and the arteries.

In addition to the exemplary aspects and embodiments described above, further aspects and embodiments will become apparent by reference to the figures and by study of the following detailed descriptions.

BRIEF DESCRIPTION OF THE FIGURES

Exemplary embodiments are illustrated in referenced figures. It is intended that the embodiments and figures disclosed herein are to be considered illustrative, rather than restrictive. The invention, however, both as to organization and method of operation, together with objects, features, and advantages thereof, may best be understood by reference to the following detailed description when read with the accompanying figures, in which.

Figure 1:
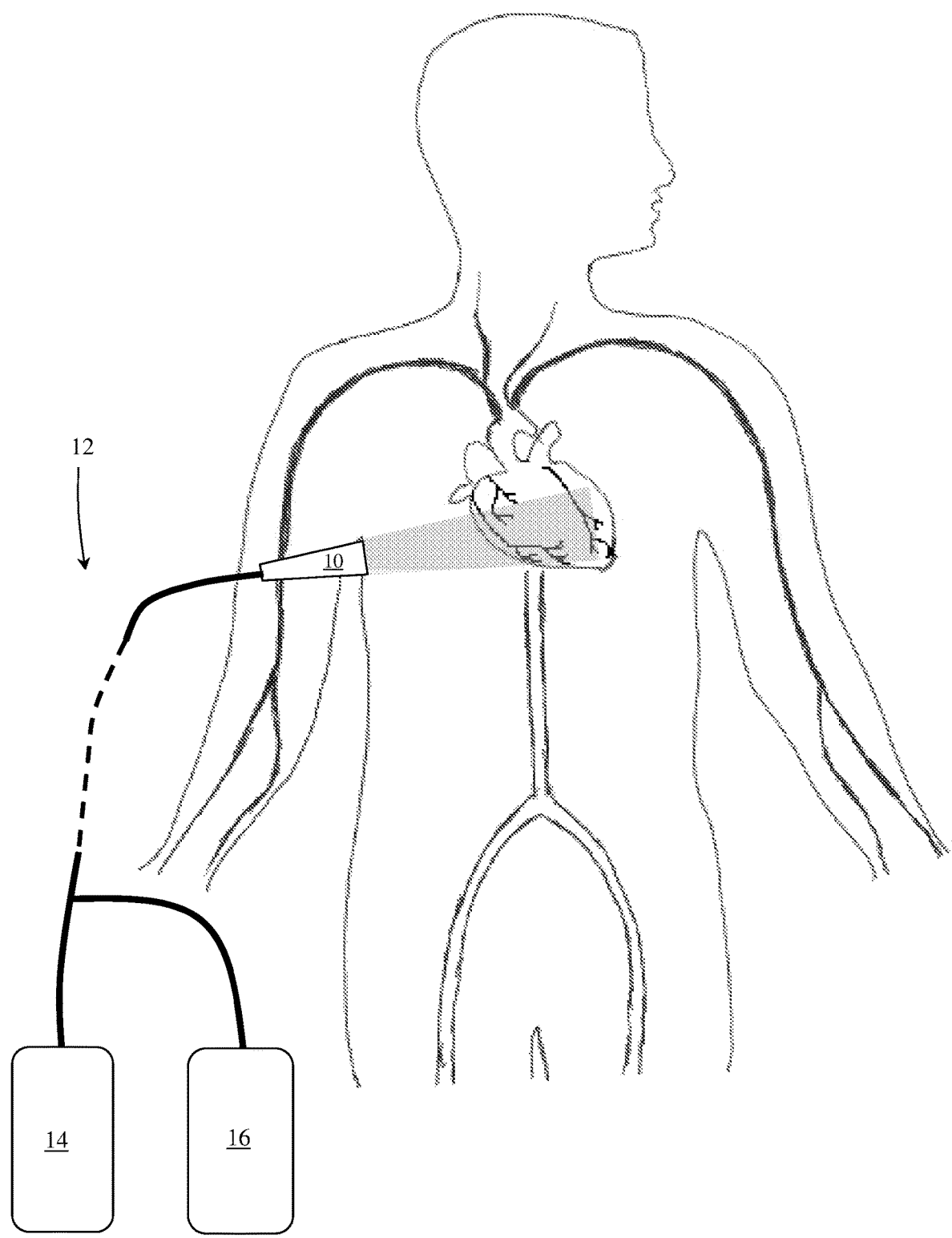
FIG. 1 schematically shows a portion of a human's cardiovascular system and an embodiment of an extracorporeal imaging device scanning portions of the cardiovascular system here at the heart.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated within the figures to indicate like elements.

DETAILED DESCRIPTION

Attention is first drawn to FIG. 1 schematically illustrating a portion of a human's cardiovascular system. An embodiment of an extracorporeal imaging device 10 may be used in accordance with an aspect of the present invention to image/scan portion of the cardiovascular system, here at the heart.

Extracorporeal imaging device 10 in one embodiment may be an opto-acoustic or photo-acoustic device arranged to screen in a non-invasive way here the cardiovascular system from outside of the body.

Imaging device 10 in its opto-acoustic embodiment may be arranged to emit/deliver laser pulses into biological tissues, which when absorbed in the tissue are converted into heat leading to ultrasonic waves that can then be detected by ultrasonic transducers within device 10 and then analyzed to produce scanned information, such as: images, 3D data such as distance from blood vessels walls and other objects within a body vasculature (or the like) representing tissue within the scanned area.

An embodiment of a system 12 for executing above mentioned imaging/scanning may include, inter alia, the extracorporeal imaging device 10, an external display 14 and a laser/opto-acoustic system 16.

Figure 2:
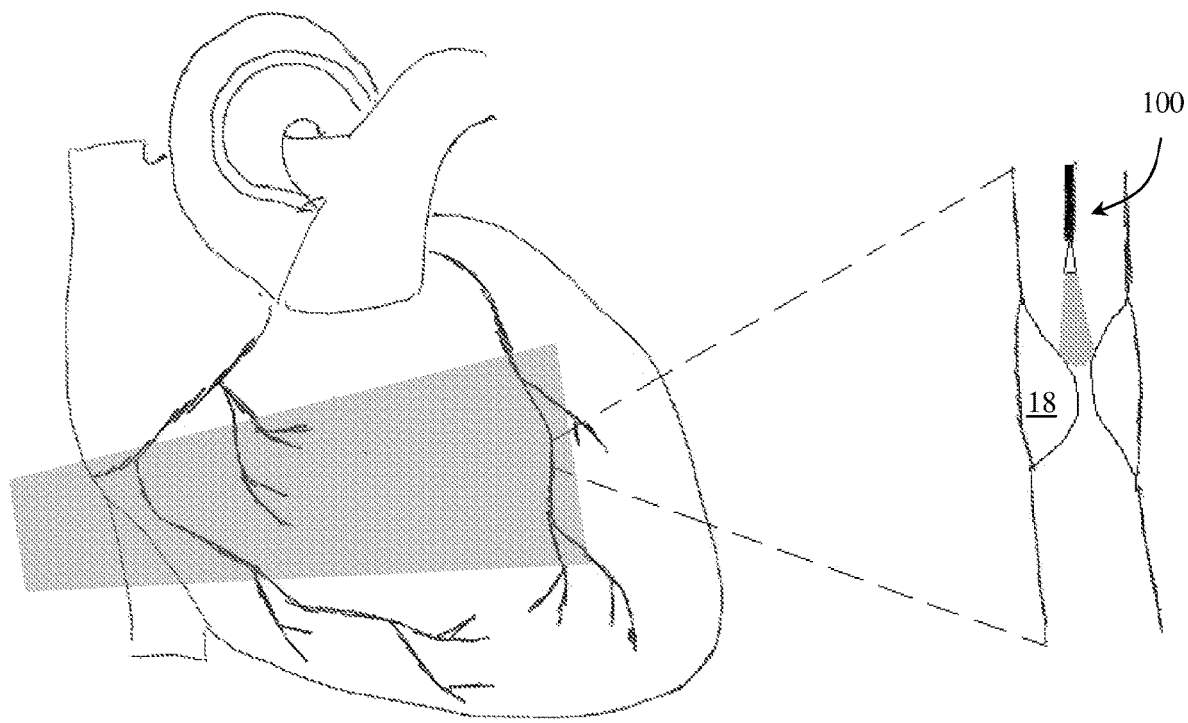
FIG. 2 schematically shows the scanned portion of the heart of FIG. 1 and an enlarged portion of the scanned area showing an artery an embodiment of an internal therapeutic device located within the artery.

Attention is drawn to FIG. 2 schematically illustrating the heart area scanned by extracorporeal imaging device 10 and in the right-hand side enlarged portion of the figure—a tip region 100 of an internal therapeutic device 100 located within an artery. In this example, internal therapeutic device 100 is embodied including an imaging utility at its tip, here generally forward-looking utility into a possible stenosis 18 substantially blocking the artery.

In certain embodiments, other imaging technologies may be utilized for extracorporeal imaging device 10. In one embodiment, such technology may include radio-wave RF imaging. A system 12 employing same may be arranged to produce images of inner arteries at relative high resolution.

Device 10 in one embodiment may be configured to include a radio antenna that emits a radio signal at a relative low frequency into an artery or any other organ. Another antenna possibly also located within device 10 may be arranged to absorb radio waves reflected back from scanned tissue.

Arteries and material clogging same may typically be transparent to radio-waves in certain frequencies—however when using relative low frequencies such arteries and material clogging same may be imaged. Using an imaging software (possibly executed at 14 or 16) inner vascular views may be reconstructed including details of narrowing's within the arteries (stenosis or the like).

By detecting reflections, preferably from different directions, scanning device 10 or system 12 in its RF configuration/embodiment—may be able to reconstruct scanned information, such as images, 3D model(s) (or the like) of a scanned artery, clog/narrowing within artery, body organ (or the like). Radio waves accordingly at relative low frequencies e.g. below 1 Khz, within any specific modulation enable human tissues and arteries imaging.

Manner in which radio waves pass through arteries (or the like) may be defined in some cases as relating to an electrical property i.e. impedance. Such impendence within arteries and tissue, may be defined as 'Bio Impedance'—and same may be seen relating to the way water and fat are present in veins, clogs and body tissues: not only their relative proportions but also more detailed properties including differentiations between materials and tissues inside the artery to enable a real time imaging and/or material density, capacitance and RF response. Within the body, thus changes in impedance may be arranged to reflect radio waves—reflections detectable by device 10 in its RF configuration/embodiment.

An antenna array within device 10 in its RF configuration—may be arranged to focus radio waves and output same waves, as well as receive them. By use of imaging software such received/detected RF waves may be used to create 3D image(s) of an artery.

Radio-wave scans, thus may accordingly be used to show/demonstrate reflections from clogs inside the artery i.e. show/detect 'surfaces' of clogs. In particular, brightness of detected RF reflection in some cases may be determined by the difference in 'bio impedance' either side of said detected 'surfaces'—resulting in radio-wave imaging according to various embodiments of the invention, being arranged to show change in impedance across a 'surface'.

In certain embodiments, such reflections may be translated into imaging to see forward within a material by means of an internal device located within a treated bodily vessel such as device 100. Same method may be used externally or internally of the body.

Conventional x-ray technology typically used for external scanning of the cardiovascular system from outside of the body, typically detects arteries by using radiopaque contrast dye that is administered into the arteries. Thus, use of technology relying on other methods for imaging may substantially eliminate use of such contrast dye in the scanning process, which may have adverse effects on the human body.

Figure 3:
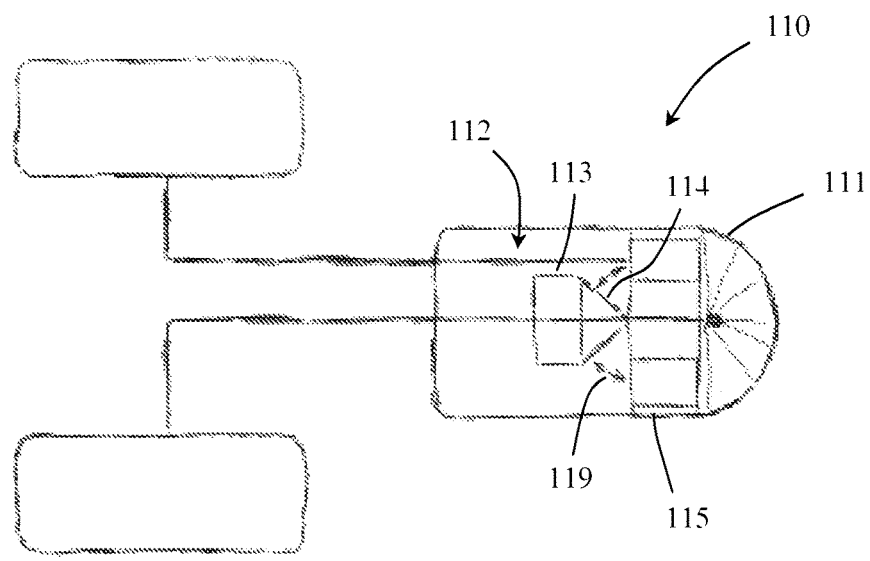
FIGS. 3 to 5 schematically illustrate various embodiments of imaging arrangements possible used on or in cooperation with internal therapeutic devices located within the artery.
Figure 4:
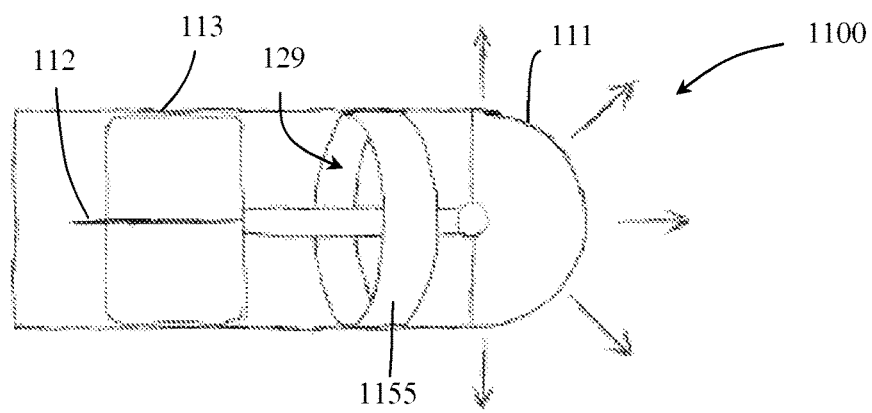
Figure 5:
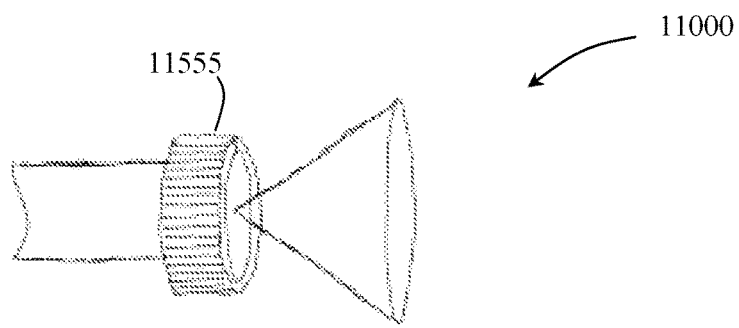

Attention is drawn to FIGS. 3 to 5 illustrating possible components of an imaging device 110, 1100, 11000 (respectively) such as that integrated or fitted to internal device 100. While from hereon configurations may be described with respect to internal device 100, it is to be understood that same may equally apply to the above-mentioned external device 10. For example, laser characteristics, optical fiber characteristics and/or transducer parameters—described with respect to internal device 100 may also apply to the external device 10.

Device 110, 1100, 11000 may be arranged to scan within a bodily vessel, possibly using photo-acoustic or laser-acoustic devices similar to those used on external device 10. Such photo-acoustic or laser-acoustic device may be fitted e.g. to a tip of a guide wire or catheter and may be arranged to visualize scanned tissues or material a few centimeters ahead e.g. into an occluded artery. Such internal scanning may be performed at the same time that scanning from outside of the body of e.g. same internal device screening may be performed.

The discussed imaging device(s) may include a dome shaped end 111 for smooth inner artery navigation and may include, inter alia, three main units: an optical fiber 112, an ultrasonic transducer unit 113, and a scanning mirror unit 114 movable/tiltable by micro-motor units.

Possibly, optical fiber 112 may be a single strand of multimode optical fiber—e.g. 0.22 NA, 365 μm core diameter, BFL22-365 of Thorlabs Inc; or a 0.25 NA, 250 μm core diameter, BFL25-250 of Thorlabs Inc, or a generic GPJ83-1 fiber optic (or the like). Laser pulses may be arranged to be delivered through such fiber optic for urging laser-acoustic imaging.

Possibly, a ring-shaped focused ultrasonic transducer (such as 115 in FIG. 3, or 1155 in FIG. 4, or 11555 in FIG. 5)—may be arranged to detect both laser and ultrasonic pulse-echo signals. The optical fiber and the ultrasonic transducer may be coaxially aligned so that the optical illumination and acoustic detection overlap to optimize the sensitivity.

A mechanically rotated mirror 114, optionally a dielectric-coated fused silica mirror, with possibly a 45°-deflected reflection surface—may serve as a component of the scanning mechanism (i.e. so-called 'scanning mirrors'). The mirror may reflect both the laser light and acoustic waves and perform rotational scanning at a B-scan frame of e.g. about ~4 Hz, driven by a geared micromotor.

A possible liquid medium (de-ionized water) may fill a sealed inner cavity of an embedment of an endoscope/device and provide acoustic coupling between the probe's imaging window (e.g. 111) and the transducer (e.g. 115). In order to provide an in-air working environment, a micromotor arranged to urge movements 119 (e.g. tilt) at the mirrors 114 may optionally physically be isolated from the liquid medium. Torque required to rotate the mirror may be transferred through magnetic coupling of the mirror and the micromotor.

Frames securing e.g. the fiber, mirror and transducer may be from metallic materials such as stainless steel or brass. The imaging window may be formed from an optically and acoustically transparent biopolymer tube with a wall thickness of about ~100 μm. The rigid metallic frames may be sheathed with another biopolymer tube (~35 μm thickness) in order, inter alia, to fix optional electric wirings that may be used in at least certain embodiments.

A system for either internal (i.e. imaging from within a bodily vessel) or external (i.e. imaging internal organs such a bodily vessel or the like, from outside of the body)—may employ a laser-acoustic or opto-acoustic scanning comprising of a Laser Acoustic, transducer, mirrors that may be controlled by micromotors and electronic circuitry.

The entire system may be controlled by an embedded control software that may also enable 2D and 3D imaging e.g. of an artery and blockages. Sub systems may include micromotor driver circuit, Laser system, an ultrasonic pulser-receiver and its amplifier, a data acquisition (DAQ) card, and a system computer for controlling and recording signals. In addition, such computer may be used for displaying images using image processing proprietary software.

Laser acoustic based imaging in one non-binding example, may be facilitated by laser pulses (e.g. of about 644 nm, ~20 ns pulse width) from a tunable dye laser (Cobra HRR, Sirah—Lasertechnik GmbH), pumped by a solid-state circuitry, diode-pumped laser, where such pulse may be guided by the optical fiber and emitted through a central hole 129 of the ultrasonic transducer.

After exiting the fiber, the laser beams may then be directed by the 'scanning mirror(s)' towards the artery tissue and blockages to generate photo-acoustic waves. The photo-acoustic waves that propagate to the scanning mirror may be reflected by the same mirror, sent to the ultrasonic transducer, to be converted into electrical signals.

These signals may be amplified by the ultrasonic pulser-receiver, and digitally recorded by a DAQ card. A proprietary software may be used to convert such signals into a 2D and 3D imaging of the inner artery and blockages. In addition since signals are penetrating blockages, a 3D image may be constructed using software.

In a possible ultrasonic pulse-echo imaging mode, electric pulses generated by the ultrasonic pulser-receiver may be sent to the transducer, where the electric pulses may be converted into acoustic pulses. The ultrasonic transducer may be thus configured to capture reflected acoustic waves such as in conventional ultrasonic imaging.

A micromotor in at least certain non-binding examples—may be arranged as a three-stage gear head with a gear ratio of about 254 to 1. Such micromotor may communicate with a driver circuit via electric wiring; where e.g. two wires may be arranged to supply a DC voltage, one wire control of direction, and a fourth wire transmission of motor's angular position-encoded signal to the driver circuit.

For each full rotation of the motor, the motor's shaft and the scanning mirror may rotate by about ~1.42° and the driver circuit may generate a corresponding TTL signal. The driver circuit's voltage may be kept at a constant value of about ~3.2 V, and the resulting rotational speed of the scanning mirror may be about ~4 Hz. Since TTL signal may be used to trigger each subsystem with a different time delay produced by the delay generator, all sequences may be synchronized by this TTL signal.

Ultrasonic transducer used for determining the spatial resolution possibly for both photoacoustic and ultrasonic imaging may be arranged tin certain cases as tested to include a piezoelectric-element of about ~2.5 mm in diameter. For adequate signal sensitivity and high spatial resolution with such restricted element size, in some cases a focused ultrasonic transducer may be utilized, possibly by using a single crystal as a piezoelectric-material, which has high longitudinal coupling coefficients (k33)>90%, and targeted a center frequency of around 45 MHz.

Acoustic focusing in some cases may be achieved by attaching a plano-concave plastic acoustic lens to the flat surface of the ultrasonic transducer. The plastic acoustic lens may be fabricated by molding polyester resin.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

Further more, while the present application or technology has been illustrated and described in detail in the drawings and foregoing description, such illustration and description are to be considered illustrative or exemplary and non-restrictive; the technology is thus not limited to the disclosed embodiments. Variations to the disclosed embodiments can be understood and effected by those skilled in the art and practicing the claimed technology, from a study of the drawings, the technology, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures can not be used to advantage.

The present technology is also understood to encompass the exact terms, features, numerical values or ranges etc., if in here such terms, features, numerical values or ranges etc. are referred to in connection with terms such as "about, ca., substantially, generally, at least" etc. In other words, "about 3" shall also comprise "3" or "substantially perpendicular" shall also comprise "perpendicular". Any reference signs in the claims should not be considered as limiting the scope.

Although the present embodiments have been described to a certain degree of particularity, it should be understood that various alterations and modifications could be made without departing from the scope of the invention as hereinafter claimed.

The invention claimed is:

1. A system for scanning organ system(s) in a human's cardiovascular system,
   the system comprising an extracorporeal opto-acoustic scanning device for scanning from outside of the body that comprises a laser and a transducer, wherein the laser being arranged to emit laser pulses towards and/or into the organ system(s) and the transducer being arranged to detect acoustic waves received back from the organ system(s) for imaging the organ system(s), wherein scanning of organ system(s) is performed substantially without administrating contrast material into a human's vasculature, and
   the system comprising in addition an internal device for being placed within the human's cardiovascular system and the extracorporeal opto-acoustic device being arranged to detect by returning acoustic waves at least portions of the internal device when inside the organ system, and
   wherein the at least portions of the internal device detectable by the extracorporeal opto-acoustic device comprise tailored markers in the form of bodily tissue for enabling detection via the transducer of specific regions within the internal device by returning acoustic waves from the markers.

2. The system of claim 1 and comprising an external display for displaying scanned data.

3. The system of claim 2, wherein the scanned data is displayed as 2D and/or 3D data.

4. The system of claim 1, wherein the internal device comprises an internal opto-acoustic scanning device for internally scanning the organ system.

5. The system of claim 4, wherein the internal opto-acoustic scanning device is at a tip of the internal device.

6. The system of claim 5, wherein the internal device is a catheter or a guidewire.

7. The system of claim 5, wherein the internal opto-acoustic scanning device comprises forward and/or sideways visualization into or within the vasculature.

8. The system of claim 1, wherein the internal device comprises tools for performing treatment actions in an artery.

9. The system of claim 8, wherein treatment actions in an artery comprise at least partially cleaning and opening plaque and/or total occlusion within an artery.

10. The system of claim 1, wherein the tailored markers are implanted within and/or upon the internal device.

11. The system of claim 1, wherein human's cardiovascular system is the heart.

12. A method for scanning a human's cardiovascular system, more preferably the heart, substantially without administrating contrast material into the system, the method comprising the steps of:
    providing an extracorporeal opto-acoustic scanning device for scanning from outside of the body that comprises a laser and a transducer,
    providing an internal device placed within the human's cardiovascular system,
    urging the laser to emit laser pulses towards and/or into the cardiovascular system, and
    utilizing the transducer to detect acoustic waves received back from the cardiovascular system in order to image the cardiovascular system and the internal device placed within the cardiovascular system,
    wherein the pulses are of about 644 nm in length and/or about 20 ns pulse width, and
    wherein the internal device comprises tailored markers in the form of bodily tissue for enabling detection.

13. The method of claim 12, wherein the internal device comprises tailored markers scannable by opto-acoustic technology.

* * * * *